United States Patent [19]

Rettenmaier et al.

[11] Patent Number: 5,143,840

[45] Date of Patent: Sep. 1, 1992

[54] SUBSTANTIALLY PURIFIED PROTEOLYTIC ENZYME FROM BACILLUS SPEC. USNI 4828 METHOD OF MAKING AND USING IT

[75] Inventors: Hansjoerg Rettenmaier, Gruenstadt; Andreas Kreimeyer, Speyer; Johannes Perner, Neustadt; Paul Diessel, Mutterstadt, all of Fed. Rep. of Germany

[73] Assignee: BASF Aktiengesellschaft, Ludwigshafen, Fed. Rep. of Germany

[21] Appl. No.: 499,376

[22] PCT Filed: Oct. 4, 1989

[86] PCT No.: PCT/EP89/01163

§ 371 Date: May 29, 1990

§ 102(e) Date: May 29, 1990

[87] PCT Pub. No.: WO90/04022

PCT Pub. Date: Apr. 19, 1990

[30] Foreign Application Priority Data

Oct. 11, 1988 [DE] Fed. Rep. of Germany ....... 3834550

[51] Int. Cl.$^5$ .......... C12N 9/54; C12N 1/00; C11D 17/00

[52] U.S. Cl. .......... 435/221; 435/832; 252/174.12

[58] Field of Search .......... 435/221, 832; 252/174.12

[56] References Cited

U.S. PATENT DOCUMENTS 3,674,643 7/1972 Aunstrup et al. .......... 435/221
4,480,037 10/1984 Ichishima et al. .......... 435/221

Primary Examiner—Douglas W. Robinson
Assistant Examiner—Mike Meller
Attorney, Agent, or Firm—Keil & Weinkauf

[57] ABSTRACT

A substantially purified proteolytic enzyme isolated from a culture of Bacillus spec. DSM 4828 which has a molecular weight of 27,000 daltons, an optimum pH of 12, an optimal temperature of 60° C. and which can be used in a detergent composition.

3 Claims, No Drawings

SUBSTANTIALLY PURIFIED PROTEOLYTIC ENZYME FROM BACILLUS SPEC. USNI 4828 METHOD OF MAKING AND USING IT

The present invention relates to a novel proteolytic enzyme, to the preparation thereof and to the use thereof as a detergent additive.

Proteolytic enzymes of high proteolytic activity in the alkaline range are already known; cf. U.S. Pat. No. 3,674,643, U.S. Pat. No. 4,480,037 and NL-A-72/07,050. These enzymes, however, are not particularly suitable for low-temperature detergents.

The present invention provides a proteolytic enzyme which is isolable from a Bacillus spec. which was accepted for deposit on Sep. 15, 1988, as deposit DSM 4828, at the International Depositary Authority, Deutsche Sammlung von Mikroorganismen und Zellkulturen GmbH, Mascheroder Weg 1 b, D-3300 Braunschweig, Germany, as established under the Budapest Treaty on the International Recognition of the Deposit of Microorganisms for the Purposes of Patent Procedure. The proteolytic enzyme has an amino acid composition of Asx 12.1%, Thr 4.8%, Ser 7.9%, Glu 6.9%, Pro 5.2%, Gly 12.9%, Ala 12.0%, Cys 0.3%, Val 7.9%, Met 3.2%, Ile 4.2%, Leu 6.5%, Tyr 4.9%, Phe 1.4%, His 3.6%, Lys 1.9% and Arg 4.0% and an amino-terminal amino acid sequence of Gln-Thr-Val-Pro-Cys-Gly-Ile-Pro-Tyr-Ile-Tyr-Ser-Asp-Val-Val-His-Arg-Gln-Gly-Tyr-Phe-Gly-Asn-Gly-Val, whose molecular weight is about 27,000 and whose isoelectric point is at pH 8.5.

The amino acid composition was determined by total hydrolysis of the protein by the Moore and Stein method. The molecular weight was determined by SDS gel electrophoresis.

The novel enzyme is preparable by growing the microorganism Bacillus spec. DSM 4828 in a nutrient medium and isolating the enzyme from the culture broth.

The choice of nutrient medium for growing the microorganism is not critical. It is possible to use nutrient media which contain carbon sources, nitrogen sources, inorganic salts and possibly small amounts of trace elements and vitamins. The nitrogen sources used can be inorganic or organic nitrogen compounds or materials which contain these compounds. Examples are: ammonium salts, nitrates, corn steep liquor, yeast autolyzate, soybean flour, yeast extract and potato starch. The carbon sources used can be sugars, such as glucose, sucrose or α-amylase hydrolyzed starch, polyols such as glycerol or else organic acids such as acetic acid or citric acid. Examples of inorganic salts are the salts of calcium, magnesium, manganese, potassium, zinc, copper, iron and other metals Suitable anions for the salts are in particular phosphate and carbonate ions. The mixing ratio of the nutrients mentioned depends on the nature of the fermentation and is decided from case to case. The growth conditions are optimized in respect of yield. Preferred growth temperatures are 32°–40° C. The pH of the medium is maintained at 7–10.5, preferably 8–10. In general, an incubation of 30–50 h is sufficient. In this time, the maximum amount of the desired product builds up in the medium.

The enzyme is separated from the culture broth in a conventional manner. The broth is centrifuged or filtered to separate off the microorganisms and insoluble material. To prepare solid enzyme products, the enzyme is precipitated for example by the addition of water-miscible organic solvents or inorganic salts such as sodium sulfate or ammonium sulfate to the filtrate. After precipitation, the enzyme is separated off by filtration or centrifuging. The filter residue obtained is then dried.

The growth of Bacillus spec. DSM 4828 succeeds under aerobic conditions.

The novel enzyme is very highly suitable for the manufacture of detergents for use at 20°–40° C. In addition, it is very stable, for example in the presence of bleaching agents, surfactants and chelating agents.

EXAMPLE 1

Isolation of Microorganism

The microorganism which produces the alkaline protease was isolated from a soil sample by a method for selecting alcalophilic bacilli (K. Horikoshi, T. Akiba/Alcalophilic Microorganisms/Japan Scientific Societies Press Tokyo). The bacterial strain DSM 4828 grows on media which contain either 0.1 M of pH 9–10 carbonate buffer or an approximately 2 M solution of NaCl.

The taxonomic studies on the strain DSM 4828 were carried out in accordance with The Prokaryotes/chapter 135/Springer Verlag. The basic medium used for the physiological tests was nutrient base medium. Solid nutrient bases are obtained by the addition of 1.8% of agar. The agar was added immediately prior to sterilization, but sterile carbonate solution was added to the end concentration of 1% (w/v) only shortly before the pouring of the agar into Petri dishes.

The microorganism DSM 4828 is aerobic and spore-forming. It must be considered of the genus Bacillus and has the following properties:

Cell morphology: vegetative cells have a diameter of from 0.5 to 0.8 μm and a length of 3 to 4 μm.
Sporangie: sometimes appear somewhat thickened.
Spores: 0.3–0.5 μm and 0.8–1 μm; oval; subterminal to central.
No growth at 50° C.
No growth at 4° C.
Optimum growth at 35°–37° C.
Gram stain: positive in all growth phases.
Anaerobic growth: no anaerobic growth in aerobic agar.
Catalase: positive.
Acetoin formation: negative.
Reduction of nitrate to nitrite: negative.
Hydrolysis of starch: negative.
Hydrolysis of casein: positive.

EXAMPLE 2

Growth of Microorganism Bacillus DSM 4828

The following medium was used:

|  | g/l |
|---|---|
| Maltose | 75 |
| Potato starch | 50 |
| Corn steep liquor | 25 |
| $K_2HPO_4$ | 1 |
| $MgSO_4 \cdot 7 H_2O$ | 0.2 |
| $CaCl_2$ | 0.02 |

The constituents of the medium were dissolved in 90% of the final volume. The pH of the solution was then adjusted with dilute sodium hydroxide solution to 8.5, and the solution was sterilized at 120° C. for 1 hour. After sterilization, the pH of the medium was adjusted to 9.5 with 15% strength sodium carbonate solution. The seed culture was obtained by seeding 400 ml of NB medium pH 8.5 to which 2.0 ml of 15% strength sodium carbonate solution had been added after 20 minutes' sterilization at 120° C. with the microorganism Bacillus spec. DSM 4828.

The seed culture was incubated on a shaker at 37° C. for 24 hours.

The medium was inoculated at 37° C. and pH 9.5 with 5 parts by volume of the seed culture per 100 parts by volume of medium. The main growth was carried out at 37° C. in 10 l stirred fermenters of 8 l capacity. The speed of the fitted paddle stirrer was 500 revolutions per minute, and the aeration rate was 1 volume of air per minute to a volume of fermentation broth. The pH of the nutrient base was not readjusted in the course of fermentation and decreased to pH 8.5 in the course of the fermentation. The broth was centrifuged after 48 hours, and the centrifuged solution was found to have an enzymatic activity of 5000 alkaline Delft units (ADU)/ml.

EXMPLE 3

Enrichment of Protease From DSM 4828

The clear supernatant liquor obtained as described in Example 2 was admixed in succession with 1.1 g of $CaCl_2$ per kg and 200 g of $(NH_4)_2SO_4$ per kg of broth. The precipitated enzyme was separated off by centrifugation. After drying, 55 g of protease in powder form were obtained per kg of centrifuged broth. The enzymatic activity of the protease obtained was found to be 50 ADU/mg by the abovementioned method.

EXAMPLE 4

Purification of Protease 100 ml of cell-free fermentation broth from Example 2 were concentrated down to 10 ml in a pressure filtration chamber using a membrane having an exclusion limit of 10,000 daltons. The volume was made up twice with 5 mmol of tris/maleic acid buffer pH 6.0 to the starting volume. Cloudiness occurring in the retentate was separated off by centrifugation at 40,000 g. The enzyme concentrate thus prepared was applied to a chromatography column containing 200 ml of CM-Sepharose CL-6B (from Pharmacia/Sweden). The ion exchange gel had beforehand been carefully equilibrated with 5 mmol of tris/maleic acid buffer pH 6.0. The enzyme solution was applied to the gel at a flow rate of 10-15 ml per h. This was followed by rinsing with the abovementioned buffer until the absorbance at 280 nm, measured against the elution buffer, had dropped to below 0.05 in the eluate. At pH 6.0 the protease binds to the gel material. It was eluted by means of a linear NaCl gradient within the concentration range from 0 to 0.5 M. The total volume of salt gradient was 0.5 l, and the flow rate was 30 ml per h. The eluate was collected in fractions of 7 ml. The protease was eluted at a concentration of 0.3 M NaCl. Fractions containing proteolytic activity were combined, demineralized by means of a pressure filtration chamber and reduced to a few ml. The enzyme material thus obtained was found to be 90-95% pure in SDS gel electrophoresis and was immediately usable for determining the amino acid composition and the amino-terminal amino acid sequence.

EXAMPLE 5

Characterization of the Enzyme

To determine relative enzyme activities (activity over temperature and pH, stability in the presence of detergent-active substances), the substrate used was azocasein. Clear enzyme solutions were appropriately diluted with 20 mmol of borate/HCl buffer (pH 8.5). 0.1 ml of this enzyme solution was made up to 1.5 ml with the same buffer preheated to 25° C. The enzyme reaction was started by adding 1 ml of 1% strength azocasein solution, which had likewise been preheated to 25° C. The reaction batch was incubated at 25° C. for 10 minutes, and the reaction was stopped by adding 1 ml of 0.3 M trichloroacetic acid solution. Precipitated protein was pelletized by centrifugation, and 1 ml of the clear supernatant was admixed with 0.25 ml of 5 M NaOH by stirring. The activity was determined by measuring the absorbance at 420 nm against a control batch. The control batch had the purpose of eliminating background adsorption and was made up as follows: before addition of the azocasein substrate, 1 ml of 0.3 M trichloroacetic acid was added to the batch (0.1 ml of enzyme solution +1.4 ml of borate/HCl buffer pH 8.5). After the addition of azocasein, the batch was incubated at 25° C. for 10 minutes and then centrifuged, and 1 ml of the supernatant was admixed with 0.25 ml of 5 M NaOH. The measured difference in absorbance between enzyme batch and control batch at 420 nm was directly used as a measure of enzyme activity.

The second method used to determine proteolytic activity was the Delft method.

This method is described in GB-B-1,353,317 and was modified as follows: 0.4% of $Na_5P_3O_{10}$ was adjusted not as specified to pH 8.5 but to pH 10. The enzyme units thus determined are alkaline Delft units (ADUs) by definition.

a) The relationship between temperature and activity:

The best temperature for the protease was determined by the azocasein method using not only 20 mmol of borate/HCl buffer (pH 8.5) but also 20 mmol of borate/NaOH buffer (pH 10). The dilute enzyme solution contained 1000 ADUs/ml The protease from DSM 4828 showed optimum activity at 60° C. not only at pH 8.5 but also pH

TABLE I

| Temperature (°C.) | Relative activity (%) | |
|---|---|---|
| | pH 8.5 | pH 10.0 |
| 20 | 6.8 | 12.9 |
| 30 | 9.8 | 18.9 |
| 40 | 22.8 | 40.6 |
| 50 | 58.7 | 72.6 |
| 60 | 100 | 100 |
| 70 | 47.7 | 17.1 | b) The relationship between pH and activity:

To determine the pH/activity profile of the protease, the azocasein was modified as follows: in place of borate/HCl buffer a buffer prepared from the following components was used: tris(hydroxy)methylaminomethane, maleic acid, acetic acid and glycine, each 40 mmol. This buffer was adjusted to the desired pH. The pH of the individual reaction batches was checked by means of a pH meter.

TABLE II

| pH | Relative activity (%) |
|---|---|
| 7 | 32.1 |
| 8 | 66.5 |
| 9 | 82.5 |
| 10 | 88.1 |
| 10.5 | 90.6 |
| 11 | 94.0 |
| 12 | 100 | c) Stability in the presence of chelating agents, bleaching agents and surfactants:

The enzyme as incubated in a concentration of 1000 ADUs/ml in 20 mmol of borate/NaOH buffer pH 10.0. The incubation temperature was 50° C. and the incubation time was 30 minutes. The enzyme activity at the start of the incubation period and after 30 minutes were measured by means of the azocasein test. The detergent-active substances were used in the stated concentrations. The relative activities reported are based on the control batch in 20 mmol of borate/NaOH buffer without additions.

TABLE III

| Detergent-active component | (concentration in g/l) | Relative activity (%) |
|---|---|---|
| Sodium perborate | (1 g/l) | 89.8 |
| Tripolyphosphate | (2 g/l) | 84.8 |
| Linear alkylbenzene-sulfonate | (1.2 g/l) | 92.9 |
| (® Lutensit A-LBN 50/BASF) Fatty alcohol polyglycol ether | (0.25 g/l) | 97.7 |
| (® Lutensol A07/BASF) Soap | (0.25 g/l) | 99.3 | d) Molecular weight and isoelectric point:

The protease has a molecular weight of 27,000 as determined by SDS gel electrophoresis. By means of the method of isoelectric focusing, this enzyme is found to have an isoelectric point of pH 8.5.

e) Amino acid composition/amino-terminal amino acid sequence:

| | Mol % |
|---|---|
| Asx | 12.1 |
| Thr | 4.8 |
| Ser | 7.9 |
| Glu | 6.9 |
| Pro | 5.2 |
| Gly | 12.9 |
| Ala | 12.0 |
| Cys | 0.3 |
| Val | 7.9 |
| Met | 3.2 |
| Ile | 4.2 |
| Leu | 6.5 |
| Tyr | 4.9 |
| Phe | 1.4 |
| His | 3.6 |
| Lys | 1.9 |
| Arg | 4.0 |
| Gln—Thr—Val—Pro—Cys—Gly—Ile—Pro—Tyr—Ile—Tyr—Ser—Arg—Val—Val—His—Arg—Gln—Gly—Tyr—Phe—Gly—Asn—Gly—Val | |

EXAMPLE 5

Detergent Action

To investigate the detergent action of the protease from DSM 4828, the test fabric used was EMPA 116 (soiled with blood, milk and chinese ink) from the Eidgenössische Materialprüfungs- und Versuchsanstalt für Industrie, Bauwesen und Gewerbe, St. Gallen, Switzerland. For a washing test, pieces of 5×5 cm were cut from a visually homogeneous part of the fabric. To prepare the washing liquor, 8 g of a commercial detergent composition without enzyme were used per 1 of synthetic tap water. The synthetic water, having a hardness of 15° German hardness, was prepared in the following manner: 10 ml of a solution of 0.656% of $MgCl_2$ in distilled water were vigorously admixed with 10 ml of a solution of 2% of $CaCl_2$ in distilled water in a 1000 ml volumetric flask. The solution obtained was then admixed with 10 ml of a solution of 2.1% $NaHCO_3$ by stirring and made up to 1000 ml with distilled water. 100 ml portions of washing liquor were each introduced into 250 ml Schikane conical flasks. The enzyme was then added in an amount of 2500 d/g of detergent, in each case in multiple batches.

The conical flasks were maintained in a shaking water bath at the temperatures indicated in Table IV by heating them in the bath with shaking. A piece of clothing material was then added to each of the conical flasks which were shaken at the particular temperature for exactly 20 minutes. After washing, the wash liquor was decanted off. 150 ml of synthetic tap water were added to the conical flasks. The flasks were sealed with rubber bungs and vigorously shaken for exactly 1 minute. The pieces of clothing material were collected in a beaker and slowly rinsed therein with running water. After the last piece of clothing material had been introduced, rinsing was continued for a further 10 minutes approximately. The pieces of clothing material, which had been folded together in a white, clean towel, were then air dried in the dark. After drying, the reflectance was measured on both sides in a reflectometer against MgO as reference standard.

The wash studies were carried out in accordance with the above description at a pH of 10.5. Table IV shows the results.

TABLE IV

| Addition | Temperature (°C.) | Reflectance (%) | Increase in detergency (%) |
|---|---|---|---|
| None | 20 | 13.6 | — |
| Protease | 20 | 19.4 | 42.6 |
| None | 30 | 15.1 | — |
| Protease | 30 | 21.4 | 41.7 |
| None | 40 | 15.7 | — |
| Protease | 40 | 24.8 | 58.0 |
| None | 50 | 15.4 | — |
| Protease | 50 | 24.5 | 59.0 |
| None | 60 | 14.0 | — |
| Protease | 60 | 19.0 | 35.7 |

We claim:

1. A substantially purified proteolytic enzyme from Bacillus spec. DSM 4828, which has an amino acid composition of Asx 12.1%, Thr 4.8%, Ser 7.9%, Glu 6.9%, Pro 5.2%, Gly 12.9%, Ala 12.0%, Cys 0.3%, Val 7.9%, Met 3.2%, Ile 4.2%, Leu 6.5%, Tyr 4.9%, Phe 1.4%, His 3.6%, Lys 1.9% and Arg 4.0%, an amino-terminal amino acid sequence of Gln-Thr-Val-Pro-Cys-Gly-Ile-Pro-Tyr-Ile-Tyr-Ser-Asp-Val-Val-His-Arg-Gln-Gly-Tyr-Phe-Gly-Asn-Gly-Val, which has a pH range for protease activity of 7 to 12, with an optimal of pH 12, which has a temperature range for protease activity of 20° C. to 70° C., with an optimal activity temperature of 60° C., whose molecular weight is about 27,000 daltons and whose isoelectric point is at pH 8.5.

2. A process for preparing a proteolytic enzyme as claimed in claim 1, which comprises growing the microorganism Bacillus spec. DSM 4828 in a nutrient medium and isolating the enzyme from the culture broth.

3. A detergent composition containing an enzyme as claimed in claim 1.

* * * * *

UNITED STATES PATENT AND TRADEMARK OFFICE
CERTIFICATE OF CORRECTION

PATENT NO. : 5,143,840
DATED : September 1, 1992
INVENTOR(S) : Rettenmaier et al.

It is certified that error appears in the above-identified patent and that said Letters Patent is hereby corrected as shown below:

On title page, item [54] and col. 1, in the title,

"Spec. USNI 4828" should read --Spec. DSM 4828,--.

Signed and Sealed this

Fourteenth Day of September, 1993

Attest:

BRUCE LEHMAN

*Attesting Officer*  *Commissioner of Patents and Trademarks*